United States Patent
Shin et al.

(10) Patent No.: US 9,671,508 B2
(45) Date of Patent: Jun. 6, 2017

(54) DEVICE FOR DETECTING THERAPEUTIC PROTON BEAM EMITTED IN PENCIL BEAM SCANNING MODE

(71) Applicant: NATIONAL CANCER CENTER, Gyeonggi-do (KR)

(72) Inventors: Dong Ho Shin, Gyeonggi-do (KR); Me Young Kim, Gangwon-do (KR); Joo Young Kim, Gyeonggi-do (KR); Jae Man Son, Seoul (KR); Se Byeong Lee, Gyeonggi-do (KR); Young Kyung Lim, Gyeonggi-do (KR); Ui Jung Hwang, Gyeonggi-do (KR)

(73) Assignee: National Cancer Center, Gyeonggi-Do (KR)

( * ) Notice: Subject to any disclaimer, the term of this patent is extended or adjusted under 35 U.S.C. 154(b) by 0 days.

(21) Appl. No.: 15/108,852

(22) PCT Filed: Dec. 10, 2014

(86) PCT No.: PCT/KR2014/012116
§ 371 (c)(1),
(2) Date: Jun. 29, 2016

(87) PCT Pub. No.: WO2015/102254
PCT Pub. Date: Jul. 9, 2015

(65) Prior Publication Data
US 2016/0327658 A1    Nov. 10, 2016

(30) Foreign Application Priority Data

Dec. 31, 2013   (KR) ......................... 10-2013-0169315

(51) Int. Cl.
*G01T 1/20*   (2006.01)
*G01T 5/08*   (2006.01)
(Continued)

(52) U.S. Cl.
CPC .............. *G01T 5/08* (2013.01); *A61N 5/1043* (2013.01); *A61N 5/1075* (2013.01); *G01T 1/22* (2013.01);
(Continued)

(58) Field of Classification Search
CPC ...... G01T 1/201; G01J 3/0218; A61N 5/1064; A61N 5/1048; A61N 5/1071; A61N 5/107
See application file for complete search history.

(56) References Cited

U.S. PATENT DOCUMENTS 5,704,890 A * 1/1998 Bliss .................... A61N 5/1048
                                                        600/1
2007/0181815 A1* 8/2007 Ebstein .................... G01T 1/02
                                                        250/370.11

FOREIGN PATENT DOCUMENTS

JP       06-294871      10/1994
JP       08-015086       1/1996
(Continued)

OTHER PUBLICATIONS

International Search Report and Written Opinion issued in PCT/KR2014/012117, dated Apr. 10, 2015.

*Primary Examiner* — Kiho Kim
(74) *Attorney, Agent, or Firm* — Norton Rose Fulbright US LLP

(57) ABSTRACT

The disclosed device for detecting the position and dose distribution of a therapeutic proton beam emitted in a pencil beam scanning mode comprises: a proton beam progressing position detection unit comprising a plurality of first optical fibers arranged along the first direction and a plurality of second optical fibers arranged along the second direction which is different from the first direction; and a proton beam dose distribution detection unit comprising a plurality of optical wavelength converter, each of which comprises an optical wavelength conversion disk and an optical wave-
(Continued)

length-converting optical fibers arranged along the outer circumference of the optical wavelength conversion disk. The proton beam progressing position detection unit detects a proton beam progressing position through the arrangement of the first and second optical fibers, and the proton beam dose distribution detection unit detects a dose distribution of the proton beam progressing direction through a plurality of optical wavelength conversion disks.

12 Claims, 3 Drawing Sheets

(51) Int. Cl.
 *G01T 1/29* (2006.01)
 *A61N 5/10* (2006.01)
 *G01T 1/22* (2006.01)

(52) U.S. Cl.
 CPC ........ *G01T 1/29* (2013.01); *A61N 2005/1087* (2013.01)

(56) References Cited

FOREIGN PATENT DOCUMENTS

| | | |
|---|---|---|
| JP | 09-230053 | 9/1997 |
| JP | 10-288671 | 10/1998 |
| JP | 2851319 | 1/1999 |
| JP | 11-118933 | 4/1999 |
| JP | 2003-310590 | 11/2003 |
| JP | 2005-342514 | 12/2005 |
| JP | 2013506823 | 2/2013 |
| KR | 10-2012-0084591 | 7/2012 |
| KR | 10-2012-0085499 | 8/2012 |
| KR | 10-1320891 | 10/2013 |

* cited by examiner

DEVICE FOR DETECTING THERAPEUTIC PROTON BEAM EMITTED IN PENCIL BEAM SCANNING MODE

CROSS-REFERENCE TO RELATED APPLICATIONS

This application is a national phase application under 35 U.S.C. §371 of International Application No. PCT/KR2014/012116 filed Dec. 10, 2014, which claims priority to Korean Patent Application No. 10-2013-0169315 filed Dec. 31, 2013. The entire contents of each of the above-referenced disclosures are specifically incorporated herein by reference without disclaimer.

TECHNICAL FIELD

The present invention relates to an apparatus which detects a position and beam dose distribution of a therapeutic proton beam source, and more particularly, to a proton beam detector which precisely monitors a position and dose distribution of a therapeutic proton beam emitted in a pencil beam scanning mode in real time.

BACKGROUND ART

Generally, various irradiation methods of transmitting a proton beam generated by an accelerator such as a cyclotron or a synchrotron to a patient for radiotherapy using protons have been used. One of general proton beam transmission methods which are currently used most in proton-therapeutic institutions is a scattering mode in which a large therapeutic irradiation surface is formed by allowing protons to collide with a target of a certain material to be scattered. However, a therapeutic method using the scattering mode has several significant problems such as secondary radiation including neutrons and gamma rays generated while protons are scattered, activation of a brass shielder and a compensator formed of an acrylic material used for controlling an irradiation surface of radiation, an increase in unnecessary beam dose of a normal organ which occurs during a proton beam adjustment process using the compensator, etc.

To solve several the problems generated in the proton beam transmission method using the scattering mode, a proton therapy method using pencil beam scanning has been provided recently and will soon be utilized for patient care. The proton beam transmission method using a pencil beam scanning mode, unlike the conventional scattering mode transmission method, transmits several energy beam dose distributions to a patient for therapy using a combination of scanning magnets, and is the most advanced next generation therapeutic method capable of maximizing and optimizing cancer treatment using protons by facilitating intensity modulated proton therapy (IMPT) that has been impossible in the scattering mode. Also, since the pencil beam scanning method adjusts a beam using a combination of magnets, a scatterer and a shielder are unnecessary. Accordingly, side effects of the generation of secondary radiation caused by gamma rays and neutrons may be basically eliminated and time and cost for manufacturing a maximum of 30 or more shielders and compensators for each patient and each treatment area may be reduced.

In the proton beam transmission method using the pencil scanning mode described above, unlike a double scattering method of generating a flat beam using a lead scatterer and irradiating the same beam dose distribution, since a dose distribution includes a combination of a large number of pencil beams and an error occurs in a beam dose and a beam dose distribution transmitted to a patient when a position of one pencil beam changes, verification thereof is necessary. Particularly, there is a probability of the occurrence of an error in a moving organ. Accordingly, to reduce a dynamic uncertainty factor and to obtain an optimized treatment result, it is necessary to verify accuracy in a therapeutic beam dose of a therapeutic proton beam transmitted in a proton pencil beam scanning mode. That is, when a proton beam dose distribution and a therapeutic beam dose are not precisely determined in a human body, a therapeutic effect rapidly decreases or a beam dose is intensively transmitted even to tissue or an organ sensitive to radiation, thereby causing severe side effects to a patient.

Korean Patent Publication No. 10-2012-0085499, a prior document, discloses a conventional method of measuring a therapeutic proton beam dose. In the method of measuring a dose of a proton beam disclosed in the prior document, a beam dose is measured while optical fibers with different lengths are arranged in a water phantom while the water phantom is moving, and the method has a difficulty in being applied to measure a precise beam source position and beam dose distribution needed in a proton beam transmission method using a pencil beam scanning mode.

As described above, in the beam dose measurement in the proton-therapeutic method using a pencil beam scanning mode, unlike the conventional scattering mode, measurement using a three-dimensional water phantom is impossible and an apparatus for verifying a precise beam dose distribution has not yet been invented.

DISCLOSURE

Technical Problem

It is an aspect of the present invention to provide an apparatus for detecting a therapeutic proton beam emitted in a pencil beam scanning mode capable of improving accuracy in proton therapy by precisely detecting a position and a dose of the therapeutic proton beam emitted in the pencil beam scanning mode.

Technical Solution

One aspect of the present invention provides an apparatus for detecting a therapeutic proton beam emitted in a pencil beam scanning mode, including a proton beam progress position detector which includes a plurality of first optical fibers arranged in a first direction and a plurality of second optical fibers arranged in a second direction different from the first direction. Here, the proton beam progress position detector is arranged to allow the therapeutic proton beam emitted in the pencil beam scanning mode to penetrate a plane formed by an arrangement of the plurality of first optical fibers and a plane formed by the plurality of second optical fibers.

The direction in which the first optical fibers are arranged and the direction in which the second optical fibers are arranged may be orthogonal each other.

The proton beam progress position detector may further include a frame which fixes the first optical fibers and the second optical fibers.

The apparatus may further include a photodetector which detects light for each optical fiber included in the plurality of first optical fibers and the plurality of second optical fibers and a signal processor which calculates a progress position of the proton beam according to a position of the optical fiber at which light is detected.

Another aspect of the present invention provides an apparatus for detecting a therapeutic proton beam emitted in a pencil beam scanning mode, including a proton beam dose distribution detector which includes a plurality of optical wavelength converter each including an optical wavelength conversion disk and an optical wavelength conversion optical fiber arranged along an outer circumference of the optical wavelength conversion disk. Here, the plurality of optical wavelength converter are stacked to allow top and bottom surfaces of the optical wavelength conversion disks to face each other, and the proton beam dose distribution detector is arranged to allow a therapeutic proton beam emitted in the pencil beam scanning mode to be incident on the optical wavelength conversion disks.

The optical wavelength conversion disks may each include a blue wavelength shifting material which converts ultraviolet (UV) light into blue light.

The optical wavelength conversion optical fibers may each include a green wavelength shifting material which converts blue light into green light.

The proton beam dose distribution detector may further include light reflecting films formed on top and bottom surfaces of a structure including the optical wavelength conversion disk and the optical wavelength conversion optical fiber.

The apparatus may further include a photodetector which detects light for each of a plurality of optical wavelength conversion optical fibers and a signal processor which calculates an arrival position of the proton beam according to a position of the optical fiber at which light is detected.

Still another aspect of the present invention provides an apparatus for detecting a therapeutic proton beam emitted in a pencil beam scanning mode, including a proton beam progress position detector which includes a plurality of first optical fibers arranged in a first direction and a plurality of second optical fibers arranged in a second direction and a proton beam dose distribution detector which includes a plurality of optical wavelength converter each including an optical wavelength conversion disk and an optical wavelength conversion optical fiber arranged along an outer circumference of the optical wavelength conversion disk. Here, the proton beam progress position detector is arranged to allow a therapeutic proton beam emitted in the pencil beam scanning mode to penetrate a plane formed by an arrangement of the plurality of first optical fibers and a plane formed by the plurality of second optical fibers. The plurality of optical wavelength converter are stacked to allow top and bottom surfaces of the optical wavelength conversion disks to face each other, and the proton beam dose distribution detector is arranged to allow the therapeutic proton beam emitted in the pencil beam scanning mode to be incident on the optical wavelength conversion disks. The proton beam dose distribution detector is arranged below the proton beam progress position detector in a progress direction of the proton beam to allow the planes formed by the plurality of first optical fibers and the plurality of second optical fibers to be parallel to the top and bottom surface of the optical wavelength conversion disks.

The apparatus may further include a photodetector which detects light for each optical fiber included in the plurality of first optical fibers and the plurality of second optical fibers and for each of a plurality of optical wavelength conversion optical fibers, and a signal processor which calculates a progress position and an arrival position of the proton beam according to a position of the optical fiber at which light is detected.

Advantageous Effects

According to the present invention, the accuracy of proton therapy may be improved by precisely detecting a position and a dose of a therapeutic proton beam emitted in a pencil beam scanning mode. Accordingly, side effects generated by transmitting a proton beam to an organ of a patient that is not a target of the therapy may be minimized and the efficiency of proton therapy may be notably increased.

MODE FOR INVENTION

Hereinafter, embodiments of the present invention will be described in detail with reference to the attached drawings. However, the embodiments of the present invention may be modified into several different shapes and the scope of the present invention is not limited to the embodiments which will be described below. The embodiments of the present invention are provided to more completely explain the present invention to one of ordinary skill in the art of the present invention. Also, terms defined while describing the present invention are defined considering functions thereof in the present invention, which may vary according to the intention of those skilled in the art or conventions. Accordingly, the terms should not be understood as having meanings which limit the technical components of the present invention.

Figure 1:
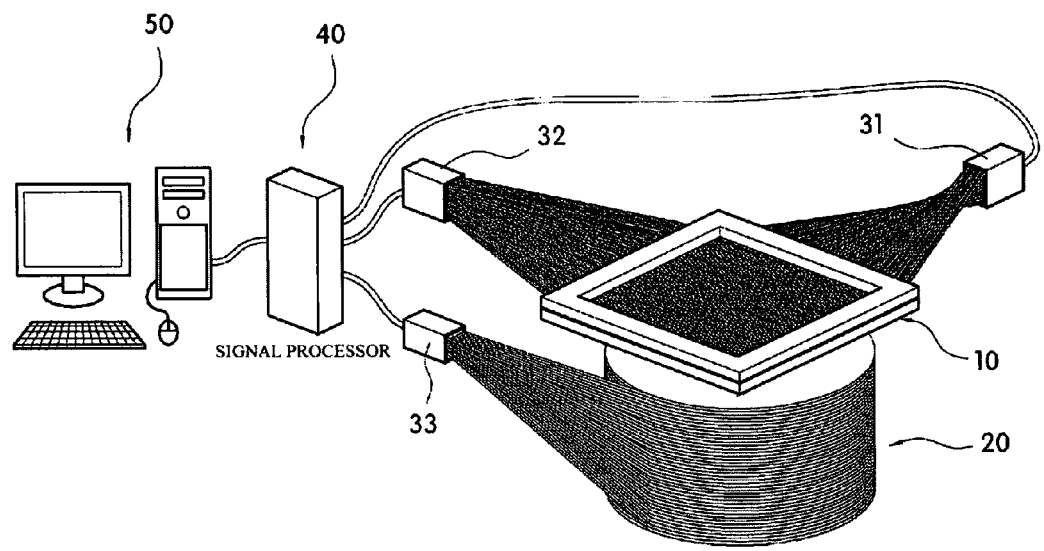
FIG. 1 is a configuration diagram of an apparatus for detecting a therapeutic proton beam emitted in a pencil beam scanning mode according to one embodiment of the present invention.

FIG. 1 is a configuration diagram of an apparatus for detecting a therapeutic proton beam emitted in a pencil beam scanning mode according to one embodiment of the present invention.

Referring to FIG. 1, the apparatus for detecting the therapeutic proton beam emitted in the pencil beam scanning mode according to one embodiment of the present invention includes a proton beam progress position detector 10 for detecting a position through which a proton beam passes and a proton beam dose distribution detector 20 for detecting a proton beam dose distribution according to the position through which the proton beam passes. In one embodiment of the present invention, the proton beam progress position detector 10 and the proton beam dose distribution detector 20 may be embodied as one of two elements depending on a selection of information to be detected.

In addition, the apparatus for detecting the therapeutic proton beam emitted in the pencil beam scanning mode according to one embodiment of the present invention may include photodetectors 31 to 33 for detecting an optical signal generated by the proton beam progress position detector 10 and an optical signal generated by the proton beam dose distribution detector 20, a signal processor 40 which calculates the position through which the proton beam passes and a proton beam dose using information on the optical signal detected by the photodetectors 31 to 33, and a display portion 50 for displaying a result of processing by the signal processor 40.

Figure 2:
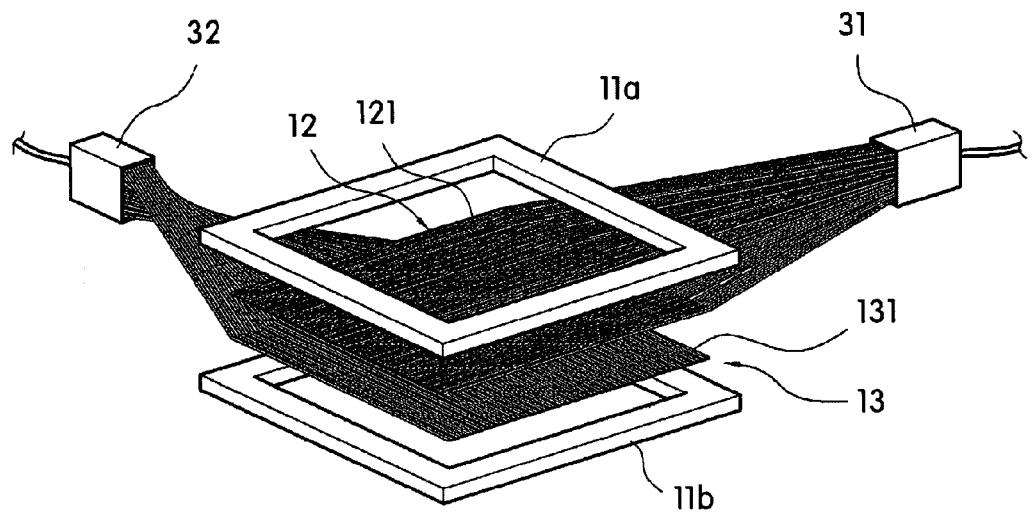
FIG. 2 is an exploded perspective view illustrating a proton beam progress position detector of the apparatus for detecting the therapeutic proton beam emitted in the pencil beam scanning mode according to one embodiment of the present invention in more detail.

FIG. 2 is an exploded perspective view illustrating the proton beam progress position detector of the apparatus for detecting the therapeutic proton beam emitted in the pencil beam scanning mode according to one embodiment of the present invention in more detail.

Referring to FIG. 2, the proton beam progress position detector 10 may include a plurality of first optical fibers 121 arranged in a first direction and a plurality of second optical fibers 131 arranged in a second direction different from the first direction. Each of the plurality of first optical fibers 121 and the plurality of second optical fibers 131 may be arranged on one plane to form one layer (hereinafter, referred to as a first optical fiber layer 12 or a second optical fiber layer 13). The first optical fiber layer 12 and the second optical fiber layer 13 may have structures which are mutually arranged on top and bottom. Also, the first direction in which the first optical fibers 121 are arranged and the second direction in which the second optical fibers 131 are arranged may be different and may be orthogonal each other. For example, at general x-y rectangular coordinates, the first optical fibers 121 may be arranged parallel to a y-axis to form x-coordinate values and the second optical fibers 131 may be arranged parallel to an x-axis to form y-coordinate values. The plurality of first and second optical fibers 121 and 131 may have tetragonal cross sections, thereby obtaining an effect of allowing arranged front surfaces to be filled with a uniform medium.

The plurality of first optical fibers 121 may be connected to one photodetector 31 and the plurality of second optical fibers 131 may be connected to another photodetector 32.

In addition, the proton beam progress position detector 10 may further include frames 11a and 11b which fix the first optical fiber layer 12 and the second optical fiber layer 13 mutually stacked at the top and bottom thereof. The frames 11a and 11b may be in contact with the top and bottom of edge areas of the first optical fiber layer 12 and the second optical fiber layer 13 to fix and expose top and bottom surfaces of a structure in which the first optical fiber layer 12 and the second optical fiber layer 13 are stacked.

Figure 3:
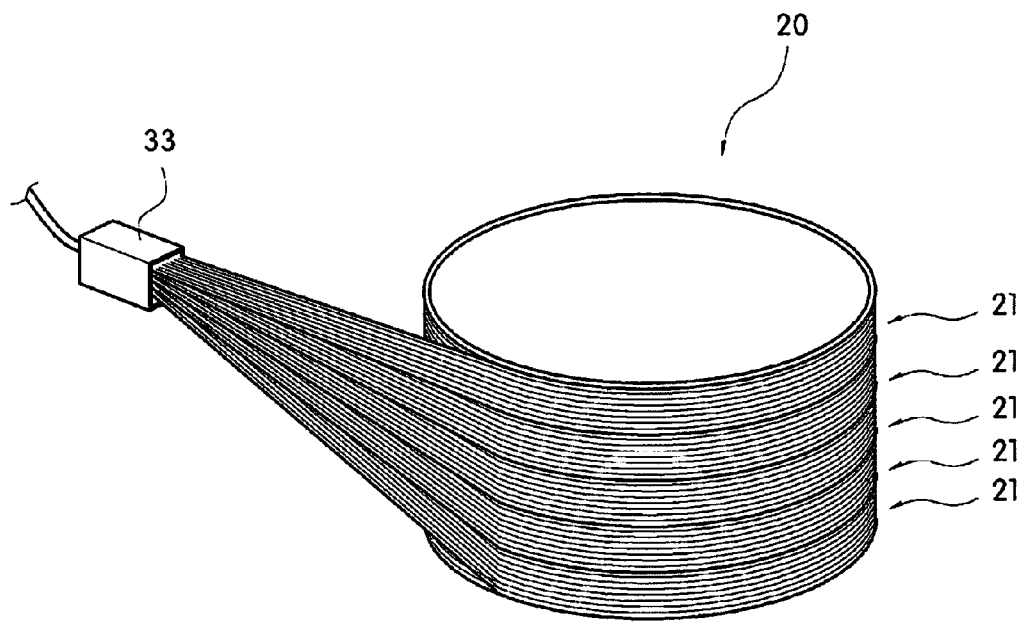
FIG. 3 is an exploded perspective view illustrating a proton beam dose distribution detector of the apparatus for detecting the therapeutic proton beam emitted in the pencil beam scanning mode according to one embodiment of the present invention in more detail.
Figure 4:
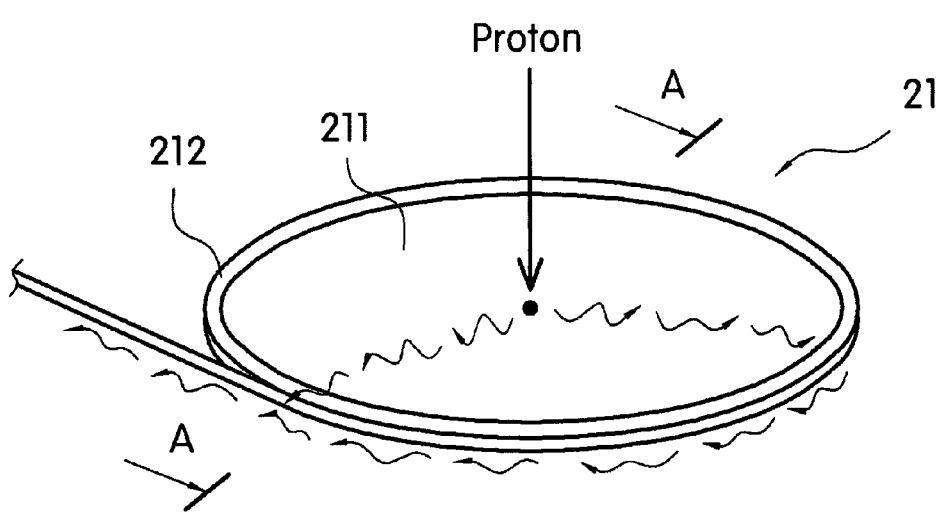
FIG. 4 is a perspective view illustrating an optical wavelength converter of the proton beam dose distribution detector shown in FIG. 3 in more detail.
Figure 5:
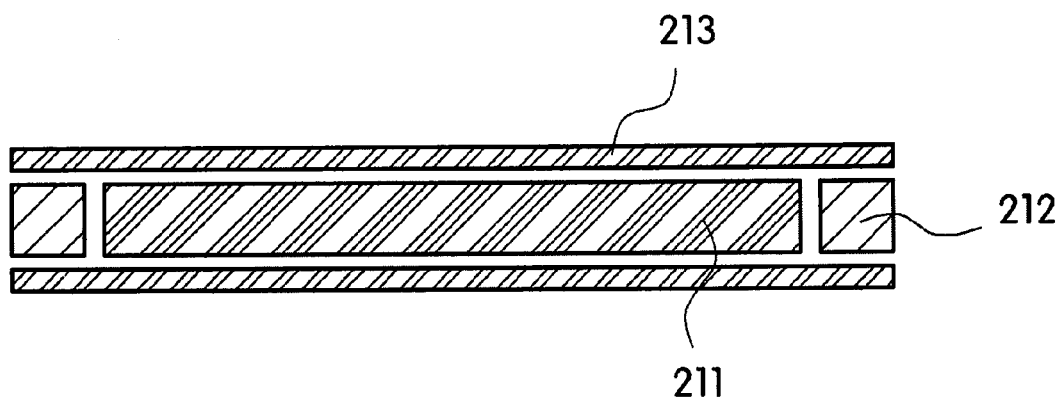
FIG. 5 is a cross-sectional view illustrating a cross section of the optical wavelength converter shown in FIG. 4 taken along line A-A'.

FIG. 3 is an exploded perspective view illustrating the proton beam dose distribution detector of the apparatus for detecting the therapeutic proton beam emitted in the pencil beam scanning mode according to one embodiment of the present invention in more detail. FIG. 4 is a perspective view illustrating an optical wavelength converter of the proton beam dose distribution detector shown in FIG. 3 in more detail. FIG. 5 is a cross-sectional view illustrating a cross section of the optical wavelength converter shown in FIG. 4 taken along line A-A'.

Referring to FIGS. 3 to 5, the proton beam dose distribution detector 20 of the apparatus for detecting the therapeutic proton beam emitted in the pencil beam scanning mode according to one embodiment of the present invention may include a plurality of optical wavelength converter 21. Each of the plurality of optical wavelength converter 21 may include an optical wavelength conversion disk 211 and an optical wavelength conversion optical fiber 212 arranged along an outer circumference of the optical wavelength conversion disk 211. Also, each of the plurality of optical wavelength converter 21 may further include light reflecting films 213 formed on top and bottom surfaces of a structure formed of the optical wavelength conversion disk and the optical wavelength conversion optical fiber.

The proton beam dose distribution detector 20 is a means for detecting a proton beam dose which pass therethrough. The plurality of optical wavelength converter 21 may be arranged in a structure which allows top and bottom surfaces of the optical wavelength conversion disk 211 to be stacked to mutually face each other. Also, the proton beam dose distribution detector 20 may be arranged to allow a therapeutic proton beam emitted in the pencil beam scanning mode to be incident on the optical wavelength conversion disk 211 of the optical wavelength converter 21. The optical wavelength conversion optical fibers 212 included in the plurality of optical wavelength converter 21 may be connected to the photodetector 33.

The plurality of optical wavelength converter 21 has a structure which is stacked in a progress direction of the proton beam. Each of the plurality of optical wavelength converter 21 may generate light when the proton beam passes therethrough. Accordingly, a position at which the proton beam arrives may be checked by checking a stacking position of the optical wavelength converter 21 at which light is generated. That is, when the proton beam dose distribution detector 20 in which the plurality of optical wavelength converter 21 are stacked is arranged below the proton beam progress position detector 10 described above to allow a plane formed by the plurality of first optical fibers 121 and the plurality of second optical fibers 131 to be parallel to the top and bottom surfaces of the optical wavelength conversion disk 211, an x-coordinate and a y-coordinate of the proton beam which progresses may be detected by the plurality of first optical fibers 121 and the plurality of second optical fibers 131 from orthogonal coordinates, and a z-coordinate at which the proton beam arrives may be determined by the plurality of optical wavelength converter 21 from the orthogonal coordinates.

The photodetectors 31, 32, and 33 connected to the first optical fibers 121 and the second optical fibers 131 of the proton beam progress position detector 10 and the optical wavelength conversion optical fibers 212 of the proton beam dose distribution detector 20 are multi-channel photodetectors which detect optical signals transmitted from the first optical fibers 121, the second optical fibers 131, and the optical wavelength conversion optical fibers 212 for each optical signal and convert detection results into electrical signals to be output. For example, the photodetector 31 may be connected to the plurality of first optical fibers 121, may detect light by forming one channel for each of the first optical fibers 121, and may output a result thereof as an electrical signal. Similarly, the photodetector 32 may detect light by forming one channel for each of the plurality of second optical fibers 131, and the photodetector 33 may detect light by forming one channel for each of the plurality of optical wavelength conversion optical fibers 212. Also, results thereof may be output as electrical signals. The photodetectors 31 to 33 described above may be embodied as multi-anode photomultiplier tubes (MAPMT), photodiode arrays, or silicon photo-multiplier arrays.

The signal processor 40 may receive and process the light detection results transmitted from the photodetectors 31 to 33 to generate information on a proton beam position and a proton beam dose distribution. In more detail, the signal processor 40 may receive and convert the electrical signals generated by detecting the light transmitted from the photodetectors 31 to 33 into digital signals and may calculate desired information (a proton beam position and/or a proton beam dose distribution) by processing the digital signals according to a preprogrammed routine. Generally, the signal processor 40 may be embodied as user-programmable data acquisition (DAQ).

The display portion 50 is an element for receiving and visually displaying the information calculated by the signal processor 40 and may be embodied as a general computer system (a desktop personal computer (PC), a notebook PC, a tablet PC, etc.) The display portion 50 may not only display the information provided by the signal processor 40, but may also be an interface unit which may provide a command of a user for requesting, processing, and correcting programs and data to the signal processor 40.

Hereinafter, an operation and effect of the apparatus for detecting a therapeutic proton beam emitted in the pencil beam scanning mode according to one embodiment of the present invention will be described in detail with reference to the attached drawings.

FIG. 1 illustrates an embodiment including both the proton beam progress position detector 10 and the proton beam dose distribution detector 20 of the apparatus for detecting a therapeutic proton beam emitted in the pencil beam scattering mode according to one embodiment of the present invention in which a proton beam source which emits a proton beam in the pencil beam scattering mode may be positioned above the proton beam progress position detector 10. The proton beam source which emits the proton beam in the pencil beam scattering mode may scan down the proton beam toward the proton beam progress position detector 10. The proton beam may pass through the proton beam progress position detector 10 and be incident on the optical wavelength converter 21 of the proton beam dose distribution detector 20 disposed therebelow.

During a process in which the proton beam emitted from the beam source in the pencil beam scanning mode passes through the proton beam progress position detector 10, the proton beam is allowed to pass through parts of the plurality of first optical fibers 121 and the plurality of second optical fibers 131 of the proton beam progress position detector 10. When the proton beam passes through an optical fiber, high energy electron beams are generated by the proton beam. The electron beams generate photons in the optical fiber due to the Cherenkov radiation effect. That is, light may be generated at the optical fiber through which the proton beam passes.

The Cherenkov radiation effect is an effect in which photons are generated in a conic shape having a certain angle with an incident beam when a charged particle penetrates a medium at a speed higher than that of light in the medium and are generated by a charged particle with more than a certain level of energy.

Cherenkov light is generated at one of the plurality of first optical fibers 121, through which the proton beam passes, and Cherenkov light is generated at one of the plurality of second optical fibers 131, through which the proton beam passes. As described above, the plurality of first optical fibers 121 and the plurality of second optical fibers 131 each form one channel and photo detection is performed by the photodetector 30. Accordingly, light is detected from the first optical fiber and the second optical fiber where Cherenkov light is generated due to the passage of the proton beam and is transmitted to the signal processor 40, the signal processor 40 may calculate a position on the proton beam progress position detector 10 through which the proton beam passes by checking positions of the first optical fiber and the second optical fiber at which the light is generated. That is, in an embodiment in which the plurality of first optical fibers 121 and the plurality of second optical fibers 131 are arranged to be orthogonal each other, the signal processor 40 may calculate the position through which the proton beam passes in the form of x-y coordinate values at an orthogonal coordinate system by checking the positions of the first optical fiber and the second optical fiber where the light is detected.

The proton beam which passes through the proton beam progress position detector 10 is incident on the proton beam dose distribution detector 20 therebelow.

Particularly, referring to FIG. 4, the proton beam passes through the optical wavelength conversion disk 211 of the optical wavelength converter 21 in the proton beam dose distribution detector 20, and as described above, light is generated in the optical wavelength conversion disk 211 due to the Cherenkov radiation effect. That is, high energy secondary electrons (177 KeV or more) which are released due to reactions between protons and a material in the optical wavelength conversion disk 211 emit Cherenkov photons. Generally, Cherenkov photons are emitted as ultraviolet (UV) rays in an area of 200 nm and allowed to have a wavelength band across almost the whole visible area. Here, since a release probability of Cherenkov light is inversely proportional to the square of a wavelength, the largest number of photons is released in a wavelength band of a UV area. Accordingly, in one embodiment of the present invention, the optical wavelength conversion disk 211 includes a blue wavelength shifting (B-WLS) material to convert UV rays into blue light to be reemitted, thereby increasing the number of photons in a measurable area. Also, a wavelength shifting material may remove direction dependency of proton beam irradiation by removing directivity of Cherenkov light emitted at a certain angle.

Cherenkov light generated by the optical wavelength conversion disk 211 is converted into blue light and may be absorbed by the optical wavelength conversion optical fibers 212 which surround the optical wavelength conversion disk 211 at the outer circumference of the optical wavelength conversion disk 211. The optical wavelength conversion optical fiber 212 may include a green wavelength shifting (G-WLS) material capable of converting the blue light absorbed by the optical wavelength conversion disk 211 into green light. The light converted into green light by the optical wavelength conversion optical fiber 212 may be provided to the photodetector 33 and inverted into an electrical signal.

Meanwhile, the light reflecting films 213 may be formed on the top and bottom surfaces of the structure formed by the optical wavelength conversion disk 211 and the optical wavelength conversion optical fiber 212 which surround the outer circumferences thereof The light reflecting films 213 may prevent loss of photons emitted outward from the optical wavelength conversion disks 211 and the optical wavelength conversion optical fibers 212 and may further increase efficiency of photodetection by inducing reflection thereinto.

As described above, the plurality of optical wavelength converter 21 have a structure which is stacked in the progress direction of the proton beam, and the optical wavelength conversion optical fibers 212 provided in the plurality of optical wavelength converter 21 each form one channel and are connected to the photodetector 33. Accordingly, the signal processor 40 may calculate the position at which the proton beam arrives by checking the position of the optical wavelength converter 21 where light is detected by the photodetector 33. That is, when the plane formed by the plurality of first optical fibers 121 and the plurality of second optical fibers 131 in the proton beam progress position detector 10 is arranged to be parallel to the top and bottom surfaces of the optical wavelength conversion disk 211 in the proton beam dose distribution detector 20, an x-coordinate and a y-coordinate of the proton beam which progresses may be detected by the plurality of first optical fibers 121 and the plurality of second optical fibers 131 from orthogonal coordinates, and a z-coordinate at which the proton beam arrives may be determined by the plurality of optical wavelength converter 21 from the orthogonal coordinates.

As described above, the apparatus for detecting a therapeutic proton beam emitted in the pencil beam scanning mode according to one embodiment of the present invention may precisely detect a position and a depth direction dose distribution of a therapeutic proton beam emitted in the pencil beam scanning mode, change it in real time, and may improve accuracy of proton therapy by reconstituting a beam dose distribution in a proton therapy area. Accordingly, side effects, etc. which may be generated by transmitting a proton beam to an organ of a patient that is not a therapeutic target may be minimized and efficiency of the proton therapy may be notably increased.

Although a few embodiments of the present invention have been shown and described, it should be appreciated by those skilled in the art that changes may be made in these embodiments without departing from the principles and spirit of the invention, the scope of which is defined in the claims and their equivalents.

The invention claimed is:

1. An apparatus for detecting a therapeutic proton beam emitted in a pencil beam scanning mode, comprising a proton beam dose distribution detector which comprises a plurality of optical wavelength converter each comprising an optical wavelength conversion disk and an optical wavelength conversion optical fiber arranged along an outer circumference of the optical wavelength conversion disk,
wherein the plurality of optical wavelength converter are stacked to allow top and bottom surfaces of the optical wavelength conversion disks to face each other, and
wherein the proton beam dose distribution detector is arranged to allow a therapeutic proton beam emitted in the pencil beam scanning mode to be incident on the optical wavelength conversion disks.

2. The apparatus of claim 1, wherein the optical wavelength conversion disks each comprise a blue wavelength shifting material which converts ultraviolet (UV) light into blue light.

3. The apparatus of claim 2, wherein the optical wavelength conversion optical fibers each comprise a green wavelength shifting material which converts blue light into green light.

4. The apparatus of claim 1, wherein the proton beam dose distribution detector further comprises light reflecting films formed on top and bottom surfaces of a structure including the optical wavelength conversion disk and the optical wavelength conversion optical fiber.

5. The apparatus of claim 1, further comprising:
a photodetector which detects light for each of a plurality of optical wavelength conversion optical fibers; and
a signal processor which calculates an arrival position of the proton beam according to a position of the optical fiber at which light is detected.

6. An apparatus for detecting a therapeutic proton beam emitted in a pencil beam scanning mode, comprising a proton beam progress position detector which comprises a plurality of first optical fibers arranged in a first direction and a plurality of second optical fibers arranged in a second direction, and a proton beam dose distribution detector which comprises a plurality of optical wavelength converter each comprising an optical wavelength conversion disk and an optical wavelength conversion optical fiber arranged along an outer circumference of the optical wavelength conversion disk,
wherein the proton beam progress position detector is arranged to allow a therapeutic proton beam emitted in the pencil beam scanning mode to penetrate a plane formed by an arrangement of the plurality of first optical fibers and a plane formed by the plurality of second optical fibers,
the plurality of optical wavelength converter are stacked to allow top and bottom surfaces of the optical wavelength conversion disks to face each other, and the proton beam dose distribution detector is arranged to allow the therapeutic proton beam emitted in the pencil beam scanning mode to be incident on the optical wavelength conversion disks, and
wherein the proton beam dose distribution detector is arranged below the proton beam progress position detector in a progress direction of the proton beam to allow the plane formed by the plurality of first optical fibers and the plurality of second optical fibers to be parallel to the top and bottom surfaces of the optical wavelength conversion disks.

7. The apparatus of claim 6, wherein the first direction in which the first optical fibers are arranged and the second direction in which the second optical fibers are arranged orthogonal.

8. The apparatus of claim 6, further comprising a frame which fixes the first optical fibers and the second optical fibers.

9. The apparatus of claim 6, wherein the optical wavelength conversion disks each comprise a blue wavelength shifting material which converts UV light into blue light.

10. The apparatus of claim 9, wherein the optical wavelength conversion optical fibers each comprise a green wavelength shifting material which converts blue light into green light.

11. The apparatus of claim 6, wherein the proton beam dose distribution detector further comprises light reflecting films formed on top and bottom surfaces of a structure including the optical wavelength conversion disk and the optical wavelength conversion optical fiber.

12. The apparatus of claim 6, further comprising:
a photodetector which detects light for each optical fiber included in the plurality of first optical fibers and the plurality of second optical fibers and for each of the plurality of optical wavelength conversion optical fibers; and
a signal processor which calculates a progress position and an arrival position of the proton beam according to a position of the optical fiber at which light is detected.

* * * * *